US010483784B2

(12) United States Patent
Konik et al.

(10) Patent No.: US 10,483,784 B2
(45) Date of Patent: Nov. 19, 2019

(54) WEARABLE, ACTIVITY-TRACKING SEX TOY, AND A METHOD FOR ITS USE

(71) Applicant: Lovely, Inc., San Francisco, CA (US)

(72) Inventors: Jakub Konik, Michalowice (PL); Tomasz Badyla, Rudy (PL)

(*) Notice: Subject to any disclaimer, the term of this patent is extended or adjusted under 35 U.S.C. 154(b) by 812 days.

(21) Appl. No.: 15/168,292

(22) Filed: May 31, 2016

(65) Prior Publication Data

US 2016/0346163 A1    Dec. 1, 2016

Related U.S. Application Data

(60) Provisional application No. 62/169,129, filed on Jun. 1, 2015.

(51) Int. Cl.
| | |
|---|---|
| A61H 19/00 | (2006.01) |
| H02J 7/02 | (2016.01) |
| A61B 5/00 | (2006.01) |
| A61B 5/11 | (2006.01) |
| H04B 7/24 | (2006.01) |
| A61B 5/024 | (2006.01) |

(52) U.S. Cl.
CPC ............ *H02J 7/025* (2013.01); *A61B 5/1118* (2013.01); *A61B 5/1123* (2013.01); *A61B 5/6847* (2013.01); *A61B 5/6898* (2013.01); *A61H 19/32* (2013.01); *A61H 19/34* (2013.01); *A61B 5/02438* (2013.01); *A61B 5/742* (2013.01); *A61B 2560/0247* (2013.01); *A61B 2562/0219* (2013.01); *A61H 2201/0188* (2013.01); *A61H 2201/5012* (2013.01); *A61H 2201/5058* (2013.01); *A61H 2201/5064* (2013.01); *A61H 2201/5079* (2013.01); *A61H 2201/5084* (2013.01); *A61H 2201/5092* (2013.01); *A61H 2201/5097* (2013.01); *A61H 2230/06* (2013.01); *H04B 7/24* (2013.01)

(58) Field of Classification Search
CPC ........ A61H 19/00; A61H 19/32; A61H 19/34; A61H 19/44; A61H 19/50; A61H 2201/5025; A61H 2201/5084; A61H 23/00
USPC .................................................... 600/38–41
See application file for complete search history.

(56) References Cited

U.S. PATENT DOCUMENTS

| | | | |
|---|---|---|---|
| 4,203,432 A | 5/1980 | Koch | |
| 4,539,980 A | 9/1985 | Chaney | |
| 4,960,113 A | 10/1990 | Seeberg-Elverfeldt | |
| 5,115,800 A | 5/1992 | Matejevic et al. | |
| 5,192,271 A | 3/1993 | Kalb et al. | |
| 5,234,402 A | 8/1993 | Osbon | |
| 5,695,444 A | 12/1997 | Chaney | |
| 5,779,621 A | 7/1998 | Chaney | |
| 6,416,461 B1 | 7/2002 | Zamar | |
| 6,705,987 B2 | 3/2004 | Anderson et al. | |
| 7,377,896 B2 | 5/2008 | Dykers, Jr. | |
| 7,678,042 B2 | 3/2010 | Jackson | |
| 8,181,654 B2 | 5/2012 | Kanno | |
| 8,308,631 B2 | 11/2012 | Kobashikawa et al. | |
| 8,449,451 B2 | 5/2013 | Dawe | |
| 8,608,644 B1 | 12/2013 | Davig | |

(Continued)

*Primary Examiner* — Samuel G Gilbert
(74) *Attorney, Agent, or Firm* — Law Office of Ilya Libenzon

(57) ABSTRACT

A wearable, activity-tracking sex toy includes a ring adapted to encircle a phallic object, at least one motion sensor, and at least one wireless communicator adapted to transmit output from the at least one motion sensor to a computing device.

15 Claims, 14 Drawing Sheets

(56) References Cited

U.S. PATENT DOCUMENTS

| | | | |
|---|---|---|---|
| 8,628,466 B2 | 1/2014 | Orten et al. | |
| D700,347 S | 2/2014 | Sedic | |
| 8,900,120 B2 | 12/2014 | Lewis et al. | |
| 8,936,544 B2 | 1/2015 | Shahoian et al. | |
| 2006/0079732 A1* | 4/2006 | Blumenthal | A61H 19/00 600/38 |
| 2006/0203889 A1* | 9/2006 | Page | H04B 1/16 375/130 |
| 2007/0179414 A1* | 8/2007 | Imboden | A61H 19/00 601/72 |
| 2013/0053630 A1* | 2/2013 | Wail | A61N 1/0521 600/38 |
| 2014/0228629 A1 | 8/2014 | Baetica et al. | |

* cited by examiner

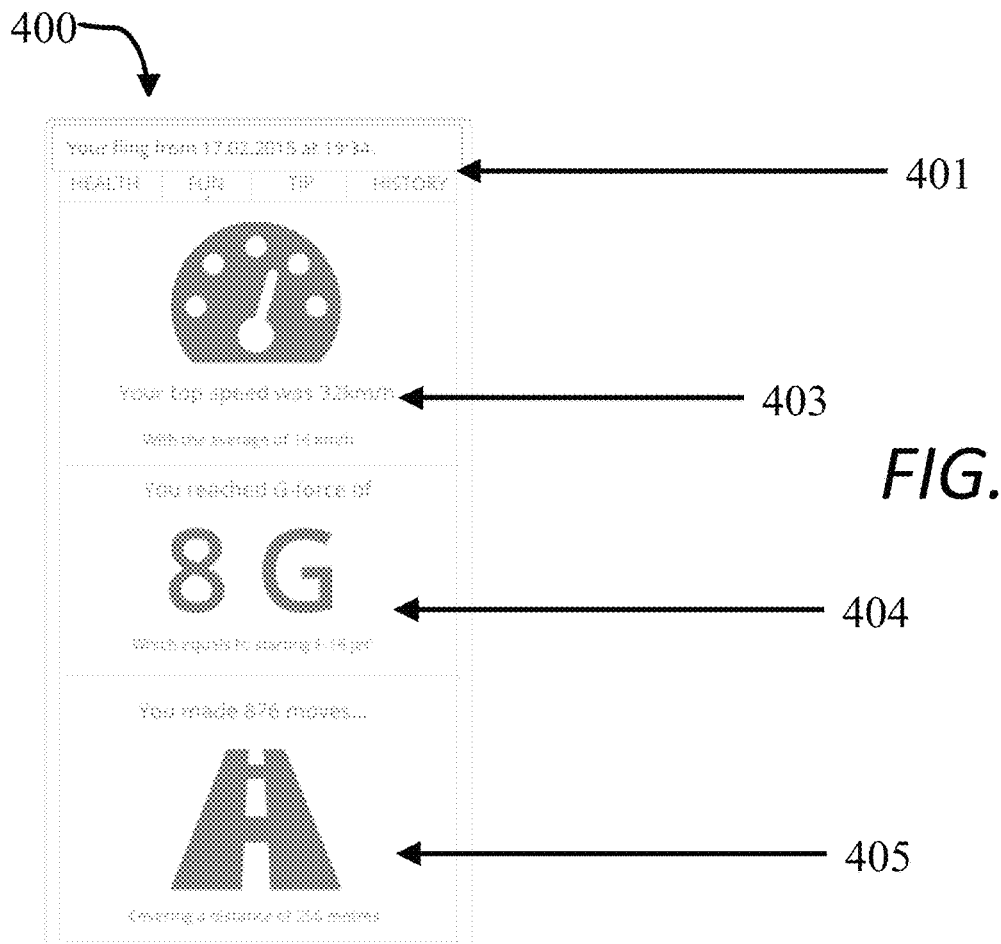
FIG. 4B
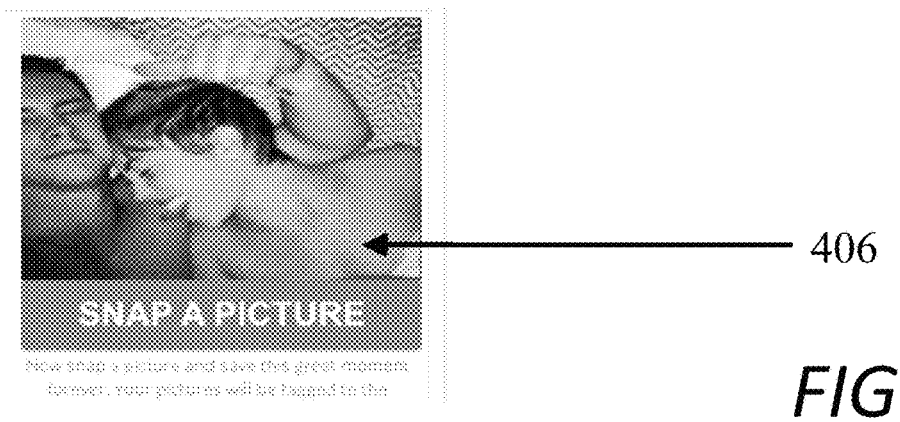
FIG. 4C
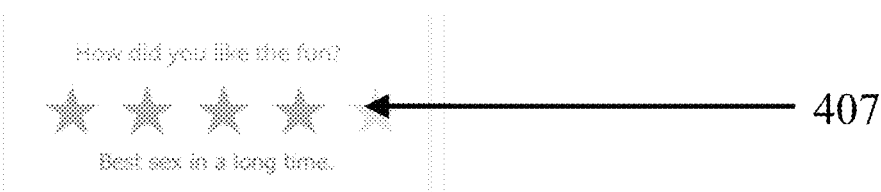

WEARABLE, ACTIVITY-TRACKING SEX TOY, AND A METHOD FOR ITS USE

TECHNICAL FIELD

Embodiments disclosed herein relate generally to sex toys, and specifically to wearable, activity-tracking sex toys.

BACKGROUND ART

Sex toys have long been used to enhance the pleasure of sexual encounters, by providing lovers with additional ways to stimulate themselves and each other. However, traditional sex toys have not thus far been able to assist couples in evaluating their own sexual needs, and in communicating those needs to each other. Likewise, although sexual activity has long been known as an effective and enjoyable form of exercise, the particular physical benefits of sexual activity have always been difficult to track and quantify; sexual activity presents unusual challenges in this respect, as many people may find it distracting to keep track of the exercise they are engaging in while attempting to focus on other aspects of sexual congress.

There is thus a need for a sex toy that can enhance communication concerning sex, and can aid in tracking the exercise benefits of sex while improving enjoyment.

SUMMARY OF THE EMBODIMENTS

In one aspect, a wearable, activity-tracking sex toy includes a ring adapted to encircle a phallic object, at least one motion sensor, and at least one wireless communicator adapted to transmit output from the at least one motion sensor to a computing device.

In a related embodiment, the at least one wireless communicator is connected to an oscillator containing elements that correct for temperature to maintain accuracy. Another embodiment includes an electrical power storage device. An additional embodiment includes a housing that completely encloses the wireless communicator, the at least one motion sensor, and the electrical power storage device, and an inductive charger enclosed in the housing and connected to the electrical power storage device. Another embodiment includes a heart rate sensor.

In another aspect, a method for tracking sexual movements includes detecting, by at least one motion sensor incorporated in a sex toy, at least one motion of the sex toy, calculating, by a processor coupled to a wireless communicator incorporated in the sex toy, at least one body movement of a user of the sex toy, based on the at least one motion of the sex toy, determining, by the wireless communicator, a connection state, and storing, by the processor, the at least one body movement, based on the detected connection state.

In a related embodiment, detecting also includes detecting a direction of acceleration of the sex toy. In another embodiment, detecting further includes detecting a degree of acceleration of the sex toy. In an additional embodiment, detecting also involves detecting a change in orientation of the sex toy. In a further embodiment, calculating also includes maintaining a number representing the current velocity of the sex toy, numerically integrating a detected acceleration to calculate a resulting velocity, and adding the resulting velocity to the number representing the current velocity. In yet another embodiment, calculating further involves comparing the at least one motion to one or more threshold values to determine that a particular sexual movement has taken place.

In another embodiment, determining further includes determining that there is no connection to the at least one computing device, and storing further includes storing the at least one body movement in memory incorporated in the sex toy. In still another embodiment, determining further involves determining that there is a connection to the at least one computing device, and storing also includes transmitting data describing the at least one body movement to the at least one computing device. An additional embodiment includes determining that a series of body movements are stored in memory of the sex toy and transmitting the stored series of body movements to the at least one computing device. A further embodiment includes saving data concerning a sexual encounter in memory during the sexual encounter and transmitting the data to the computing device when the sexual encounter concludes.

Another embodiment includes calculating, by the at least one computing device, at least one cumulative datum concerning the sexual encounter, using the at least one body movement. In an additional embodiment, calculating the cumulative datum further involves calculating the total calories burned by a user during the sexual encounter. In still another embodiment, calculating the cumulative datum also includes calculating the duration of the sexual encounter. In a further embodiment still, calculating the cumulative datum also includes calculating the top speed achieved by a user of the sex toy. An additional embodiment also involves generating, by the computing device, a user tip using at least one datum of the data concerning the at least one body movement data and the at last one cumulative datum.

Other aspects, embodiments and features of the device and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the system and method shown where illustration is not necessary to allow those of ordinary skill in the art to understand the device and method.

BRIEF DESCRIPTION OF THE DRAWINGS

The preceding summary, as well as the following detailed description of the disclosed system and method, will be better understood when read in conjunction with the attached drawings. For the purpose of illustrating the system and method, presently preferred embodiments are shown in the drawings. It should be understood, however, that neither the system nor the method is limited to the precise arrangements and instrumentalities shown.

FIG. 4B is a screenshot of an embodiment of an application;

FIG. 4C is a screenshot of an embodiment of an application;

DETAILED DESCRIPTION OF SPECIFIC EMBODIMENTS

Figure 1A:
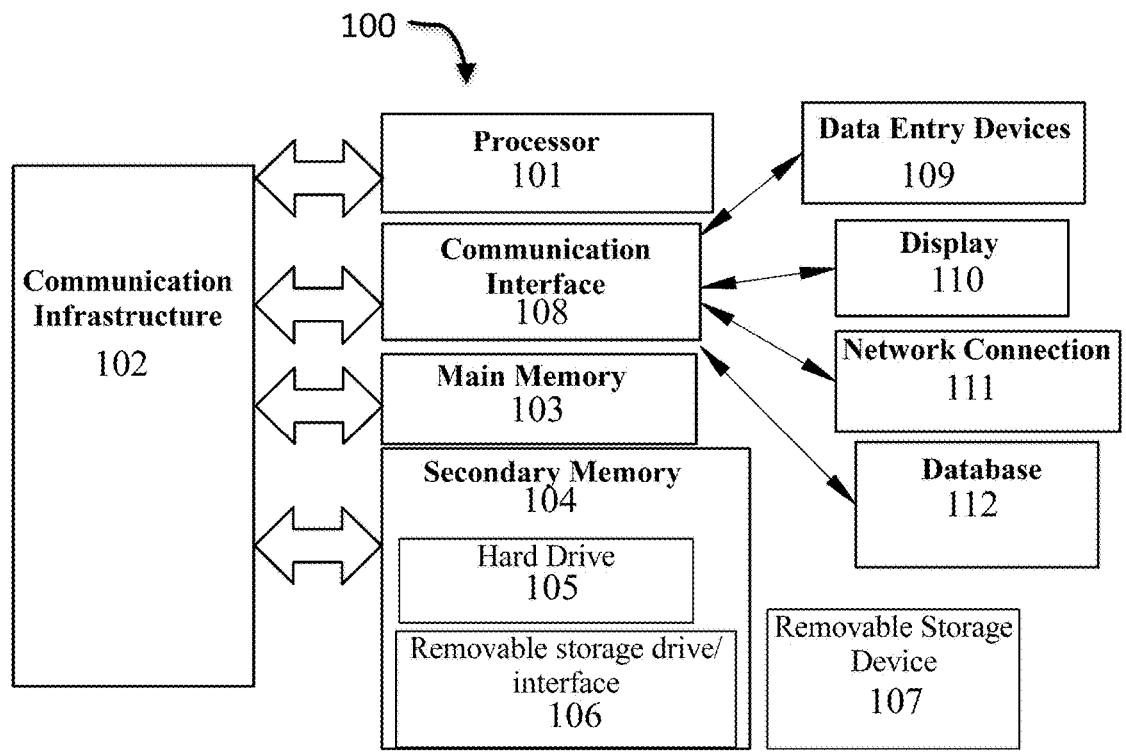
FIG. 1A is a schematic diagram depicting an example of an computing device as described herein.

Some embodiments of the disclosed system and methods will be better understood by reference to the following comments concerning computing devices. A "computing device" may be defined as including personal computers, laptops, tablets, smart phones, and any other computing device capable of supporting an application as described herein. The system and method disclosed herein will be better understood in light of the following observations concerning the computing devices that support the disclosed application, and concerning the nature of web applications in general. An exemplary computing device is illustrated by FIG. 1A. The processor 101 may be a special purpose or a general-purpose processor device. As will be appreciated by persons skilled in the relevant art, the processor device 101 may also be a single processor in a multi-core/multiprocessor system, such system operating alone, or in a cluster of computing devices operating in a cluster or server farm. The processor 101 is connected to a communication infrastructure 102, for example, a bus, message queue, network, or multi-core message-passing scheme.

The computing device also includes a main memory 103, such as random access memory (RAM), and may also include a secondary memory 104. Secondary memory 104 may include, for example, a hard disk drive 105, a removable storage drive or interface 106, connected to a removable storage unit 107, or other similar means. As will be appreciated by persons skilled in the relevant art, a removable storage unit 107 includes a computer usable storage medium having stored therein computer software and/or data. Examples of additional means creating secondary memory 104 may include a program cartridge and cartridge interface (such as that found in video game devices), a removable memory chip (such as an EPROM, or PROM) and associated socket, and other removable storage units 107 and interfaces 106 which allow software and data to be transferred from the removable storage unit 107 to the computer system. In some embodiments, to "maintain" data in the memory of a computing device means to store that data in that memory in a form convenient for retrieval as required by the algorithm at issue, and to retrieve, update, or delete the data as needed.

The computing device may also include a communications interface 108. The communications interface 108 allows software and data to be transferred between the computing device and external devices. The communications interface 108 may include a modem, a network interface (such as an Ethernet card), a communications port, a PCMCIA slot and card, or other means to couple the computing device to external devices. Software and data transferred via the communications interface 108 may be in the form of signals, which may be electronic, electromagnetic, optical, or other signals capable of being received by the communications interface 108. These signals may be provided to the communications interface 108 via wire or cable, fiber optics, a phone line, a cellular phone link, and radio frequency link or other communications channels. Other devices may be coupled to the computing device 100 via the communications interface 108. In some embodiments, a device or component is "coupled" to a computing device 100 if it is so related to that device that the product or means and the device may be operated together as one machine. In particular, a piece of electronic equipment is coupled to a computing device if it is incorporated in the computing device (e.g. a built-in camera on a smart phone), attached to the device by wires capable of propagating signals between the equipment and the device (e.g. a mouse connected to a personal computer by means of a wire plugged into one of the computer's ports), tethered to the device by wireless technology that replaces the ability of wires to propagate signals (e.g. a wireless BLUETOOTH® headset for a mobile phone), or related to the computing device by shared membership in some network consisting of wireless and wired connections between multiple machines (e.g. a printer in an office that prints documents to computers belonging to that office, no matter where they are, so long as they and the printer can connect to the internet). A computing device 100 may be coupled to a second computing device (not shown); for instance, a server may be coupled to a client device, as described below in greater detail.

The communications interface in the system embodiments discussed herein facilitates the coupling of the computing device with data entry devices 109, the device's display 110, and network connections, whether wired or wireless 111. In some embodiments, "data entry devices" 109 are any equipment coupled to a computing device that may be used to enter data into that device. This definition includes, without limitation, keyboards, computer mice, touchscreens, digital cameras, digital video cameras, wireless antennas, Global Positioning System devices, audio input and output devices, gyroscopic orientation sensors, proximity sensors, compasses, scanners, specialized reading devices such as fingerprint or retinal scanners, and any hardware device capable of sensing electromagnetic radiation, electromagnetic fields, gravitational force, electromagnetic force, temperature, vibration, or pressure. A computing device's "manual data entry devices" is the set of all data entry devices coupled to the computing device that permit the user to enter data into the computing device using manual manipulation. Manual entry devices include without limitation keyboards, keypads, touchscreens, track-pads, computer mice, buttons, and other similar components. A computing device may also possess a navigation facility. The computing device's "navigation facility" may be any facility coupled to the computing device that enables the device accurately to calculate the device's location on the surface of the Earth. Navigation facilities can include a receiver configured to communicate with the Global Positioning System or with similar satellite networks, as well as any other system that mobile phones or other devices use to ascertain their location, for example by communicating with cell towers. A code scanner coupled to a computing device is a device that can extract information from a "code" attached to an object. In one embodiment, a code contains data concerning the object to which it is attached that may be extracted automatically by a scanner; for instance, a code may be a bar code whose data may be extracted using a laser scanner. A code may include a quick-read (QR) code whose data may be extracted by a digital scanner or camera. A code may include a radio frequency identification (RFID) tag.

In some embodiments, a computing device's "display" 109 is a device coupled to the computing device, by means of which the computing device can display images. Display include without limitation monitors, screens, television devices, and projectors.

Computer programs (also called computer control logic) are stored in main memory 103 and/or secondary memory 104. Computer programs may also be received via the communications interface 108. Such computer programs, when executed, enable the processor device 101 to implement the system embodiments discussed below. Accordingly, such computer programs represent controllers of the system. Where embodiments are implemented using software, the software may be stored in a computer program product and loaded into the computing device using a removable storage drive or interface 106, a hard disk drive 105, or a communications interface 108.

The computing device may also store data in database 112 accessible to the device. A database 112 is any structured collection of data. As used herein, databases can include "NoSQL" data stores, which store data in a few key-value structures such as arrays for rapid retrieval using a known set of keys (e.g. array indices). Another possibility is a relational database, which can divide the data stored into fields representing useful categories of data. As a result, a stored data record can be quickly retrieved using any known portion of the data that has been stored in that record by searching within that known datum's category within the database 112, and can be accessed by more complex queries, using languages such as Structured Query Language, which retrieve data based on limiting values passed as parameters and relationships between the data being retrieved. More specialized queries, such as image matching queries, may also be used to search some databases. A database can be created in any digital memory.

Persons skilled in the relevant art will also be aware that while any computing device must necessarily include facilities to perform the functions of a processor 101, a communication infrastructure 102, at least a main memory 103, and usually a communications interface 108, not all devices will necessarily house these facilities separately. For instance, in some forms of computing devices as defined above, processing 101 and memory 103 could be distributed through the same hardware device, as in a neural net, and thus the communications infrastructure 102 could be a property of the configuration of that particular hardware device. Many devices do practice a physical division of tasks as set forth above, however, and practitioners skilled in the art will understand the conceptual separation of tasks as applicable even where physical components are merged.

Figure 1B:
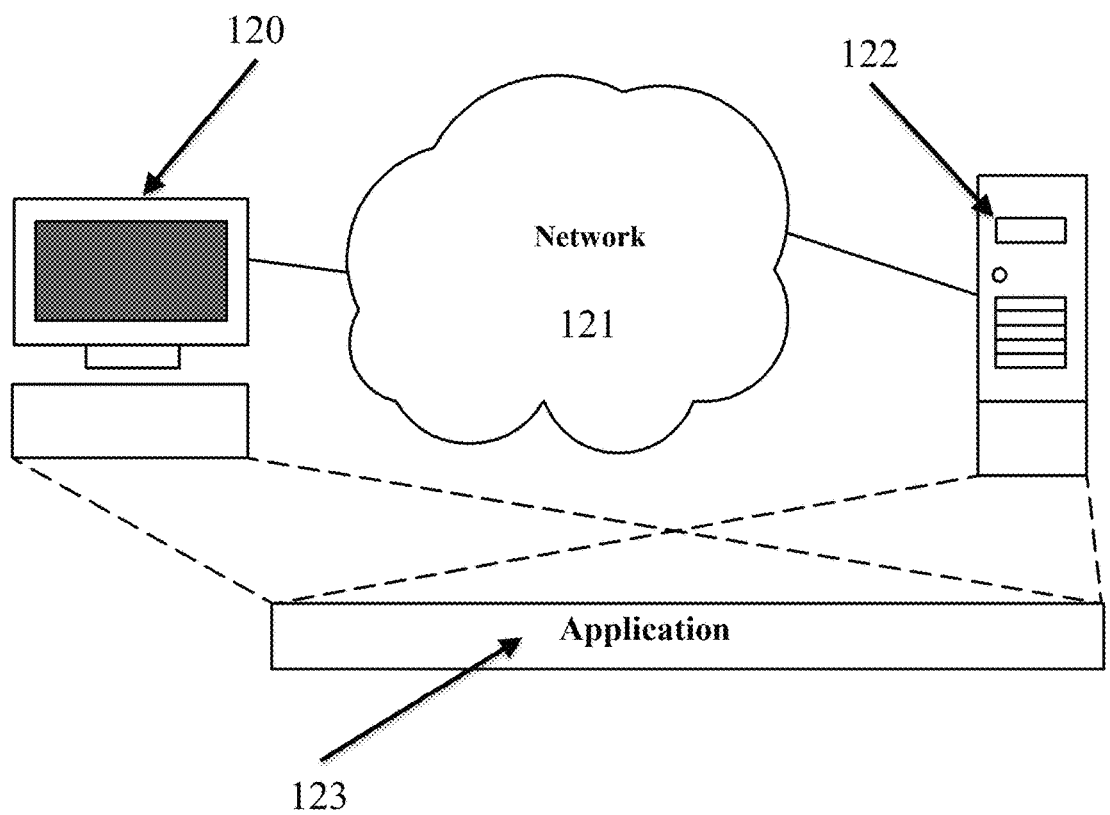
FIG. 1B is a schematic diagram of a network-based platform, as disclosed herein.

The systems may be deployed in a number of ways, including on a stand-alone computing device, a set of computing devices working together in a network, or a web application. Persons of ordinary skill in the art will recognize a web application as a particular kind of computer program system designed to function across a network, such as the Internet. A schematic illustration of a web application platform is provided in FIG. 1B. Web application platforms typically include at least one client device 120, which is an computing device as described above. The client device 120 connects via some form of network connection to a network 121, such as the Internet. The network 121 may be any arrangement that links together computing devices 120, 122, and includes without limitation local and international wired networks including telephone, cable, and fiber-optic networks, wireless networks that exchange information using signals of electromagnetic radiation, including cellular communication and data networks, and any combination of those wired and wireless networks. Also connected to the network 121 is at least one server 122, which is also an computing device as described above, or a set of computing devices that communicate with each other and work in concert by local or network connections. Of course, practitioners of ordinary skill in the relevant art will recognize that a web application can, and typically does, run on several servers 122 and a vast and continuously changing population of client devices 120. Computer programs on both the client device 120 and the server 122 configure both devices to perform the functions required of the web application 123. Web applications 123 can be designed so that the bulk of their processing tasks are accomplished by the server 122, as configured to perform those tasks by its web application program, or alternatively by the client device 120. Some web applications 123 are designed so that the client device 120 solely displays content that is sent to it by the server 122, and the server 122 performs all of the processing, business logic, and data storage tasks. Such "thin client" web applications are sometimes referred to as "cloud" applications, because essentially all computing tasks are performed by a set of servers 122 and data centers visible to the client only as a single opaque entity, often represented on diagrams as a cloud.

Many computing devices, as defined herein, come equipped with a specialized program, known as a web browser, which enables them to act as a client device 120 at least for the purposes of receiving and displaying data output by the server 122 without any additional programming. Web browsers can also act as a platform to run so much of a web application as is being performed by the client device 120, and it is a common practice to write the portion of a web application calculated to run on the client device 120 to be operated entirely by a web browser. Such browser-executed programs are referred to herein as "client-side programs," and frequently are loaded onto the browser from the server 122 at the same time as the other content the server 122 sends to the browser. However, it is also possible to write programs that do not run on web browsers but still cause an computing device to operate as a web application client 120. Thus, as a general matter, web applications 123 require some computer program configuration of both the client device (or devices) 120 and the server 122. The computer program that comprises the web application component on either computing device's system configures that device's processor 101 to perform the portion of the overall web application's functions that the programmer chooses to assign to that device. Persons of ordinary skill in the art will appreciate that the programming tasks assigned to one device may overlap with those assigned to another, in the interests of robustness, flexibility, or performance. Furthermore, although the best known example of a web application as used herein uses the kind of hypertext markup language protocol popularized by the World Wide Web, practitioners of ordinary skill in the art will be aware of other network communication protocols, such as File Transfer Protocol, that also support web applications as defined herein.

In some embodiments, the disclosed device uses built-in sensors to track movements during sex and to provide both partners with health and pleasure-related data along with simple, actionable tips that improve couples' sex life. This data and tips may be viewed after the intercourse in an application available for all partners. In some embodiments, the disclosed device and method provides users with highly personalized tips and ideas that enable them to have a better sex life. Some embodiments are profiled in a way that stimulates woman's clitoris during sex; the device may have a built-in vibration motor to enhance the stimulation. In some embodiments, the device sits on the base of a penis and slows down blood circulation inside of an erect penis, enhancing a man's erection.

Figure 2A:
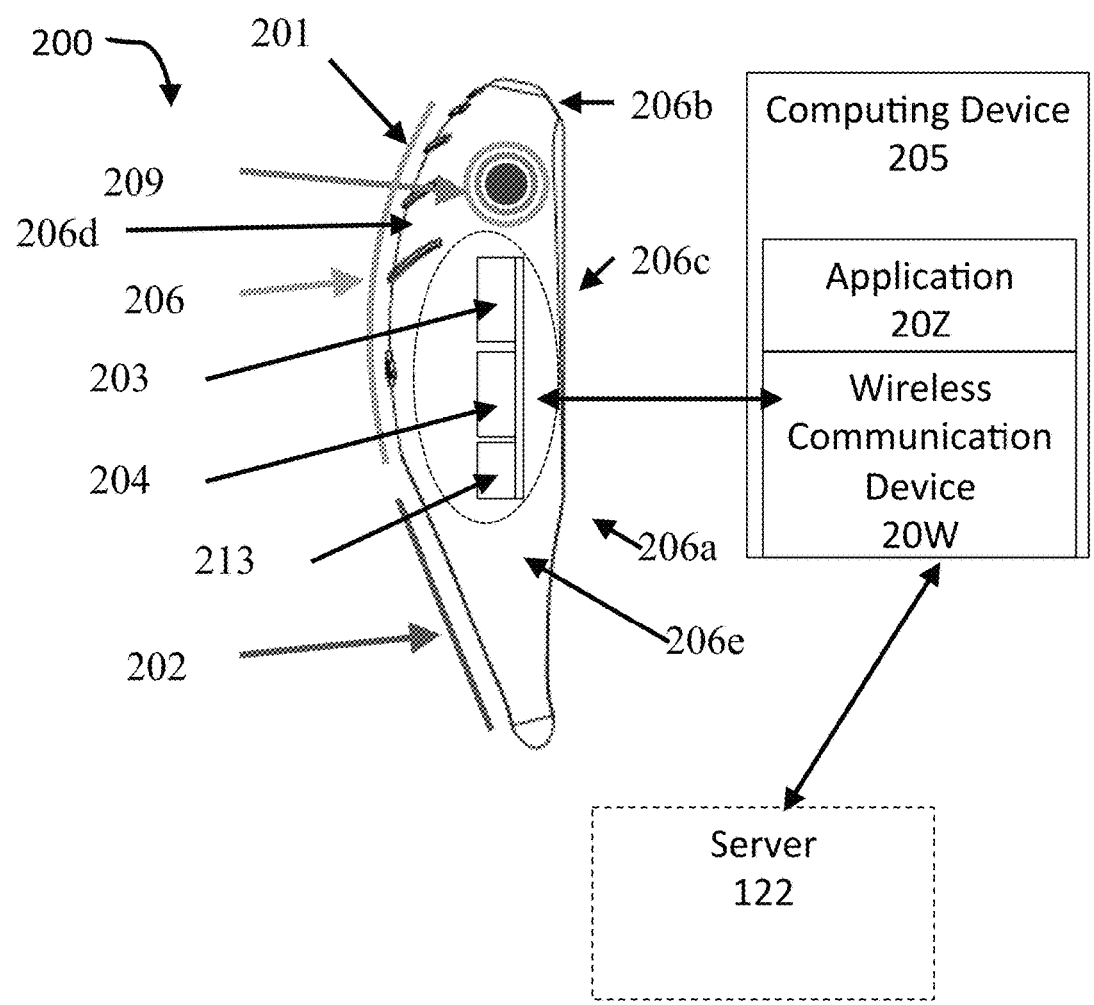
FIG. 2A is a block diagram depicting one embodiment of the disclosed system.

FIG. 2A illustrates one embodiment of a system 200. The system 200 may include a wearable sex toy 201. The wearable sex toy 201 includes a ring 202 adapted to encircle a phallic object. The sex toy 201 includes at least one motion sensor 203. The sex toy 201 includes at least one wireless communicator 204 adapted to transmit output from the at least one motion sensor to a computing device. The system 200 may include a computing device 205 configured to receive the output from the wireless communicator 204.

Referring to FIG. 2A in further detail, the sex toy 201 includes a ring 202 adapted to encircle a phallic object. The ring may be made from any material or combination of materials suitable for use as a sex toy that encircles an erect penis; for instance, the ring 202 may be constructed of any material or combination of materials typically used for sex toys that are designed to encircle an erect penis. The materials used to construct the ring 202 may be rigid materials; the materials may include metal. The materials may include a hard polymer, such as a hard plastic. In other embodiments, the materials are flexible; the materials may include leather. The materials may include a natural textile. The materials may include a synthetic textile.

In another embodiment, the ring 202 is constructed from an elastic material or combination of materials. In one embodiment, the material or combination of materials making up the elastic ring 202 is elastic if the resulting ring exhibits elasticity commensurate with that of other elastic rings designed to be worn on an erect penis. For instance, the material or combination of materials may include latex. The material or combination of materials may include an elastic silicone. The materials making up the ring 202 may include hypo-allergenic materials. As a non-limiting example, the ring 202 may be constructed of body safe silicone, such as medical silicone. The medical silicone may be mixed with a plastic, such as acrylonitrile butadiene styrene (ABS).

Figure 2B:
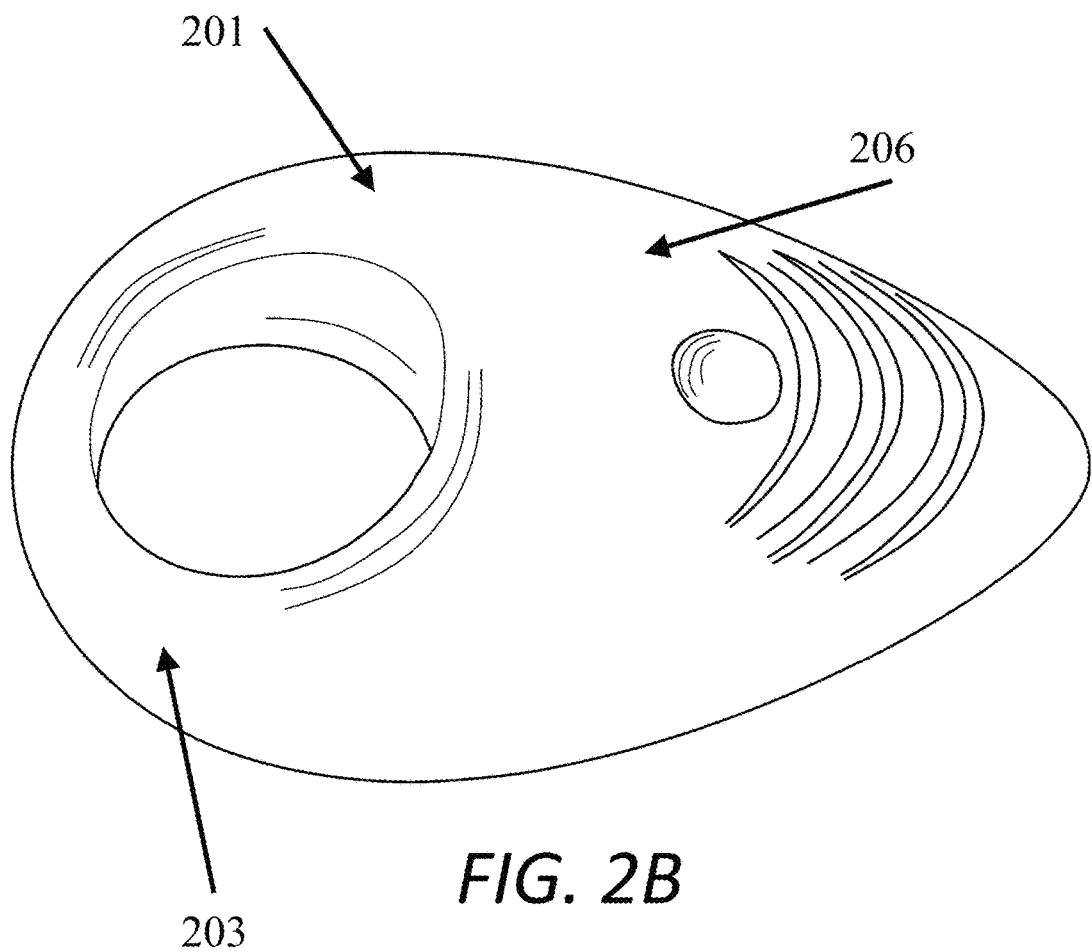
FIG. 2B is a depiction of the exterior of one embodiment of the disclosed device.

The ring 202 is adapted to encircle a phallic object (not shown). The phallic object may be a penis; in some embodiments, the phallic object is an erect penis. In other embodiments, the phallic object is another object having a substantially phallic or cylindrical form; for instance, the phallic object may be dildo or similar sex toy. The phallic object may be worn on the person of a user engaging in a sexual encounter; for instance, the phallic object may be a dildo attached to a harness to be worn on a person's pelvic region. As illustrated in FIG. 2B, the space enclosed by the ring 202 may have a substantially elliptical cross-section. In some embodiments, the space enclosed by the ring 202 is substantially circular in cross-section. The ring 202 may be rounded; for instance, the ring 202 may be substantially toroidal. In some embodiments, the substantially toroidal ring 202 can be more easily slipped on or off a phallic object; the rounded form may also make the ring 202 more comfortable to wear. The ring 202 may be sized to fit snugly around a phallic object; in some embodiments the ring 202 is sized so that it exerts inward on the phallic object. Where the phallic object is a penis, the ring 202 may exert sufficient inward pressure to restrict the flow of blood through the penis; in some embodiments, the ring 202 may aid in prolonging an erection by this means. As a non-limiting example, the ring 202 may have an interior diameter between 18 and 35 millimeters when unworn and at elastic equilibrium. The diameter may be 30 millimeters.

The sex toy 201 may include a housing 206. The housing 206 may enclose the at least one motion sensor 203. The housing 206 may enclose the wireless communicator 204. In some embodiments, the housing 206 encloses both the motion sensor 203 and the wireless communicator 204; the housing 206 may also enclose additional components electrically connected to the wireless communicator 204 or motion sensor 203. The housing 206 may be constructed of any material or combination of materials suitable for the construction of the ring 202. In some embodiments, the housing is attached to the ring. The housing may be permanently fixed to the ring. The housing and the ring may be formed as a single monolithic whole; for instance, the housing and the ring may be created together in the same molding process, as described in further detail below in reference to FIG. 5. The housing 206 may have a lower end 206a attached to the ring 202, and an upper end 206b at the farthest point of the housing from the ring. The sex toy 201 may be designed to be worn around the phallic object with the upper end 206b of the housing projecting upward to contact the clitoris of a woman when the phallic object is fully inserted in the woman's vulva. The housing may have a back surface 206c. In some embodiments, the back surface 206c is substantially flat. The housing may have a front surface 206d. The front surface may be curved. The housing 206 may have two sides 206e that connect the front surface 206d to the back surface 206c. In some embodiments, the curvature of the front surface 206d and the curvature of the two sides 206e taper from a broad, thick end at the lower end 206a of the housing to a narrower, thinner end at the upper end 206b of the housing 206; the combined perimeter of a cross section of the housing 206 and ring 202, the cross section taken parallel to the back surface 206c of the housing 206, may be substantially egg-shaped, with the broad end of the egg encompassing the perimeter at the ring 202 and the narrow end of the egg encompassing the upper end 206b of the housing 206. The housing 206 may have an internal component housing electrical elements; for instance, the electrical elements may be housed within a shell of polyacetylene (PA). FIG. 2B illustrates an exterior view of the sex toy 201 in which the housing and ring form a monolithic whole.

Figure 2C:
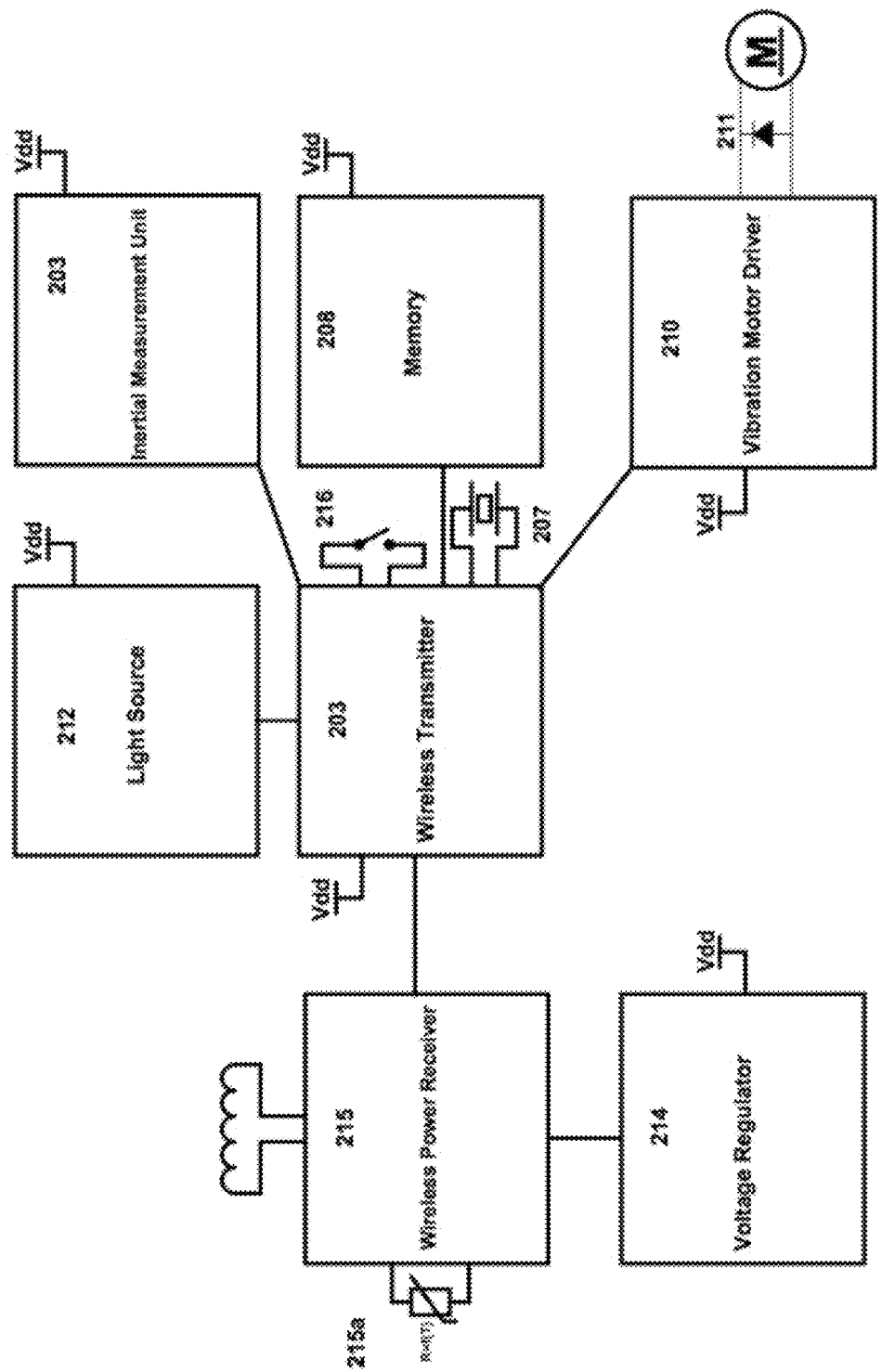
FIG. 2C is a schematic circuit diagram describing some elements of the disclosed device.

As further illustrated in FIG. 2C, the sex toy 201 includes at least one motion sensor 203. The at least one sensor 203 may include at least one accelerometer. The at least one accelerometer may include a plurality of accelerometers; for instance, the at least one accelerometer may include three accelerometers. In some embodiments the three accelerometers span three dimensions of motion; for instance each of the three accelerometers may have an axis of measurement that is not parallel to the axis of measurement of either of the other accelerometers. The axes of measurement of the three accelerometers may be mutually orthogonal. The at least one motion sensor 203 may include at least one gyroscope. The at least one motion sensor 203 may include a plurality of gyroscopes. The plurality of gyroscopes may include three gyroscopes having three axes of rotation that span three dimensions; for instance, the axis of rotation of each of the three gyroscopes may be not be parallel to the axis of rotation of either of the other two gyroscopes. The three gyroscopes may have mutually orthogonal axes of rotation. The at least one motion sensor 203 may include at least one magnetometer. The at least one motion sensor 203 may include a plurality of magnetometers. The plurality of magnetometers may include three magnetometers having three axes of measurement that span three dimensions; for instance, the axis of measurement of each of the three magnetometers may be not be parallel to the axis of rotation of either of the other two magnetometers. The three magnetometers may have mutually orthogonal axes of rotation. In some embodiments, the at least one accelerometer, the at least one gyroscope, and the at least one magnetometer are assembled together as an inertial measurement unit (IMU); the inertial measurement unit may be an integrated circuit that combines the at least one accelerometer, the at least one gyroscope and the at least one magnetometer. The IMU may include a processor that processes the input from the at least one gyroscope, the at least one accelerometer, and the at least one magnetometer. The processor may be a processor 101 as disclosed above in reference to FIGS. 1A-B. The at least one motion sensor 203 may be mounted on a printed circuit board PCB. In some embodiments, the motion sensor 203 is positioned so that one gyroscopic rotation axis is aligned with an axis that runs through the ring 202 and through the lower end 206a and upper end 206b of the housing 206, so that, for example, when the sex toy 201 is worn on the erect penis of a man, the gyroscopic rotation axis is aligned with the man's midline; in some embodiments, this alignment makes it easier for the at least one motion sensor 203 to detect the body positions of the user who is wearing the sex toy 201, as well as the user's sexual partner or partners, more accurately.

The wireless communicator 204 may be connected to the at least one sensor 202. In some embodiments, the wireless communicator 204 includes a processor. The processor may be a processor 101 as described above in reference to FIGS. 1A-B. The wireless communicator 204 may include a transceiver for communication with the computing device 205. The transceiver may be configured to communicate using any electromagnetic frequency. For instance, the transceiver may communicate in the 2.4-2.485 GHz range, like BLUETOOTH transceivers following protocols as promulgated by Bluetooth SIG, Inc. of Kirkland, Wash.

The wireless communicator 204 may be coupled to an oscillator 207. The oscillator 207 may be a precision oscillator; in some embodiments, the oscillator 207 is a crystal oscillator. The wireless communicator 204 may use the crystal oscillator 207 to correct a clock of the wireless communicator 204. In some embodiments, the crystal oscillator 207 contains elements that correct for temperature to maintain the accuracy of the oscillator 207 across temperature ranges. The elements may include one or more thermistors. The wireless communicator 204 may be coupled to a memory 208. The memory 208 may be a memory 103, 104 as disclosed above in reference to FIGS. 1A-B. In some embodiments, the memory is a solid-state memory. The memory 208 may be a flash memory. The memory 208 may have a capacity of 16 MB.

As illustrated in FIG. 2A, the sex toy 201 may include a vibrator 209. The vibrator 209 may be located near the top end 206b of the housing. In some embodiments, the location near the top end 206b of the housing places the vibrator in close proximity to a woman's clitoris when the phallic object is placed in her vagina. As shown in FIG. 2C, the vibrator may be controlled by a transistor 210. In some embodiments, the transistor 210 is a MOSFET. The gate or base of the transistor 210 may connect to a processor; in some embodiments, the wireless communicator 204 is connected to the gate or base of the transistor 210. The wireless communicator 204 may thus control the power from a power source to the vibrator 209 using the transistor 210. In some embodiments, the sex toy 201 includes a protection diode 211 that protects other circuit elements from the high voltage generated by the vibrator 209 as a result of the vibrator's high inductance. In some embodiments, the protection diode 210 is connected across the terminals 209a-b that connect to the vibrator. The protection diode 210 may be a Schottky diode. In some embodiments, a processor incorporated in the sex toy 201 removes motor noise from the vibrator 209 using a digital low-pass filter; in some embodiments, the wireless communicator 204 implements the digital low-pass filter. The algorithm may be another digital noise filtering algorithm.

The sex toy 201 may include a light source 212. In some embodiments, the light source 212 is encapsulated within the housing 206; the housing 206 may be sufficiently translucent to allow the light from the light source 212 to be visible from outside the housing 206. The light source 212 may be an electrical light source. In some embodiments, the light source 212 includes one or more electroluminescent devices; for instance, the light source 212 may include at least one light-emitting diode (LED). As a non-limiting example, the light source may include two LEDs. In some embodiments, the light source 212 is controlled by one or more terminals of a processor; for example, the light source 212 may be controlled by one or more terminals of the wireless communicator 204. In one embodiment, the wireless communicator 204 uses the light source 212 to provide feedback for the user; for instance, the light source 212 may be used to indicate that the sex toy 201 is collecting data. The light source 212 may be used to indicate that the sex toy 201 is charging. The light source 212 may be used to provide the user with an incentive to use the sex toy 201, as described in further detail below in connection with FIG. 5.

In some embodiments, as shown in FIG. 2A, the sex toy 201 includes a battery 213. The battery 213 may include one cell, or the battery 213 may include a plurality of cells. The battery 213 may be a rechargeable battery; for instance, the battery 213 may be a lithium polymer battery. The battery 213 may supply power to the other components of the sex toy 201; for instance, the battery 213 may supply power to the at least one motion sensor 203, the wireless communicator 204, the vibrator 209, and the light source 212. As shown in FIG. 2C, the battery 213 may provide power by way of a voltage regulator 214. The voltage regulator 214 may maintain the voltage provided to the components of the sex toy 201 at a constant level amenable for use by the components. For instance, where the battery 213 has a voltage of approximately 3.7 V, the voltage regulator 214 may draw current from the battery as necessary to maintain a 3.3 V voltage level. In some embodiments, where some or all electronic elements are mounted on a printed circuit board, the battery may be mounted to the back of the printed circuit board.

Figure 2D:
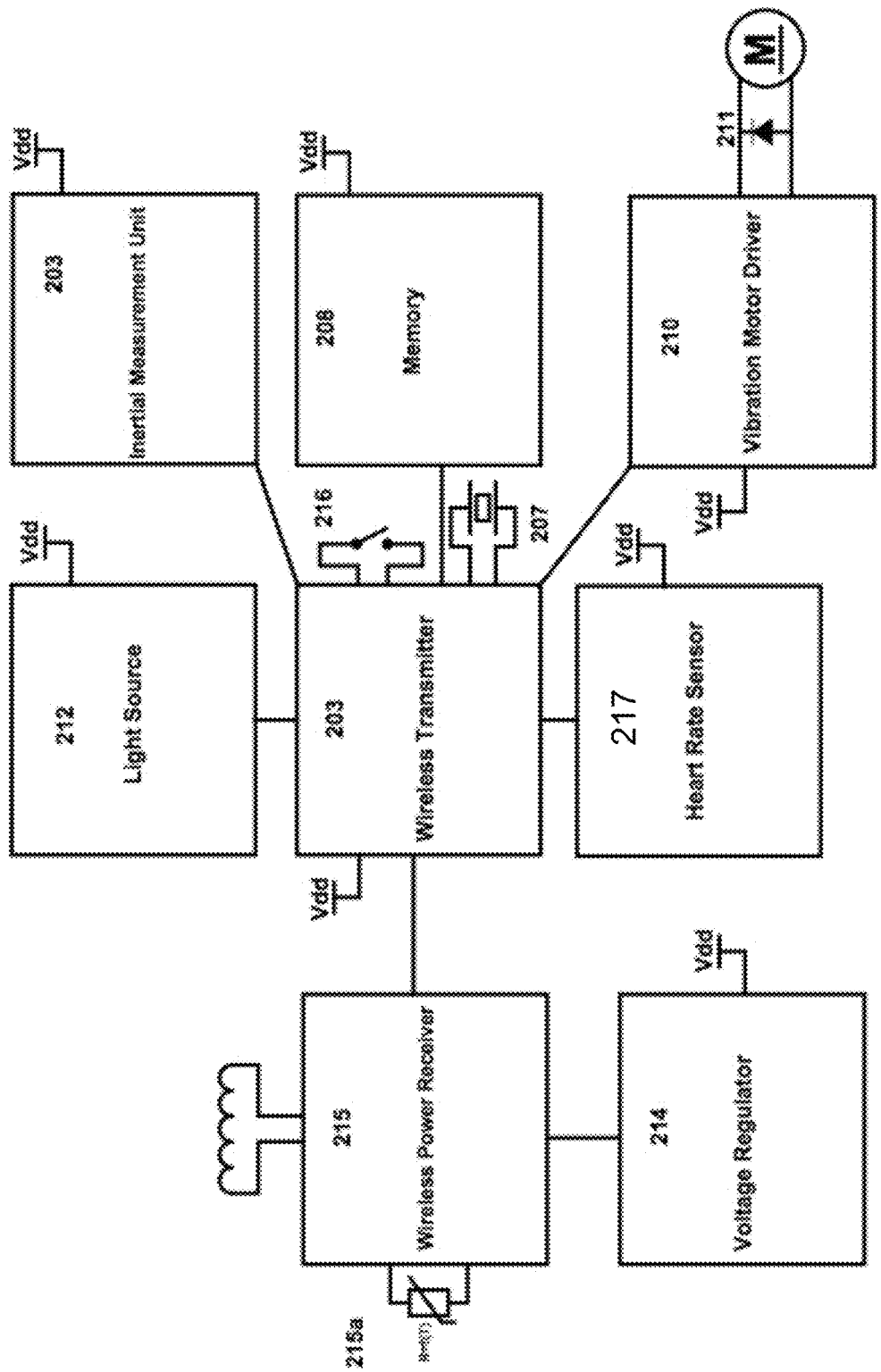
FIG. 2D is a schematic circuit diagram describing some elements of the disclosed device.
Figure 3A:
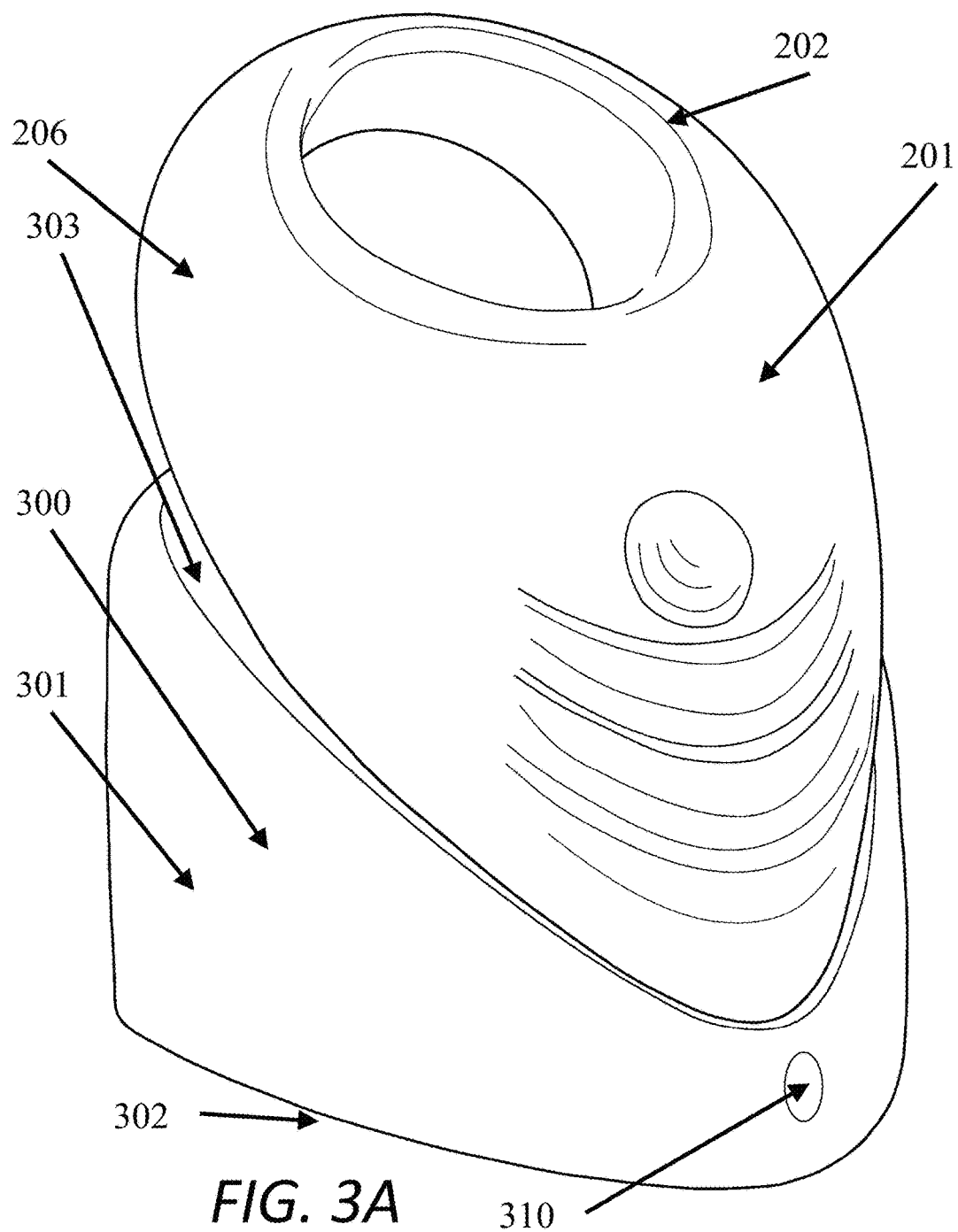
FIG. 3A depicts an embodiment of a docking station for the disclosed device.
Figure 3B:
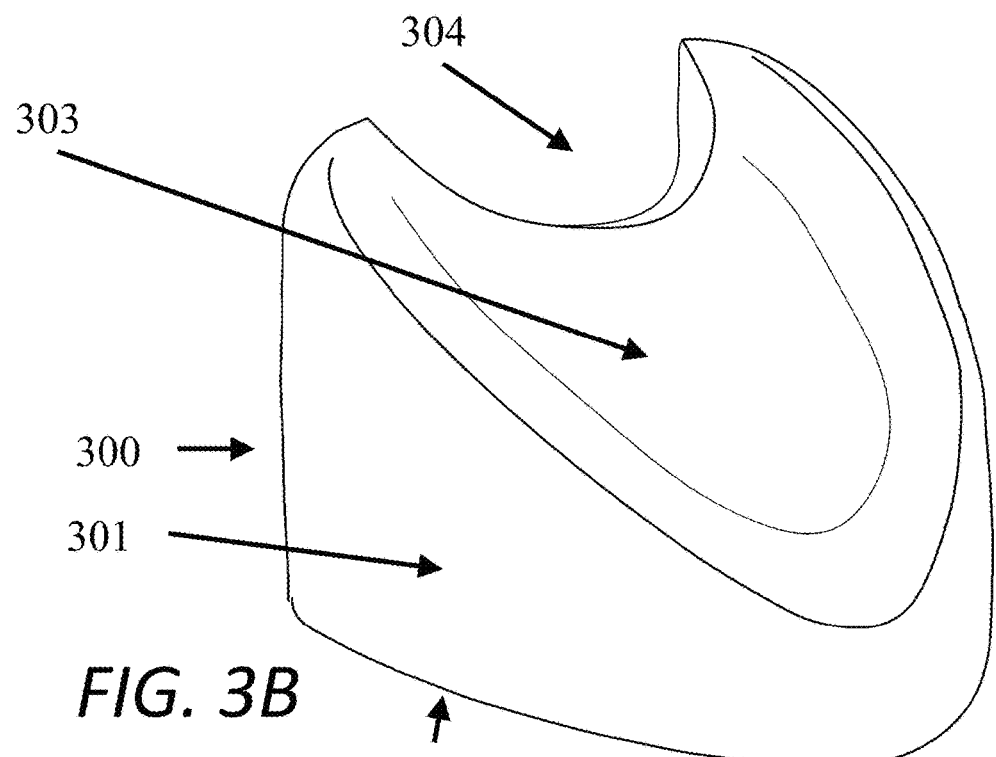
FIG. 3B depicts an embodiment of a docking station for the disclosed device.
Figure 3C:
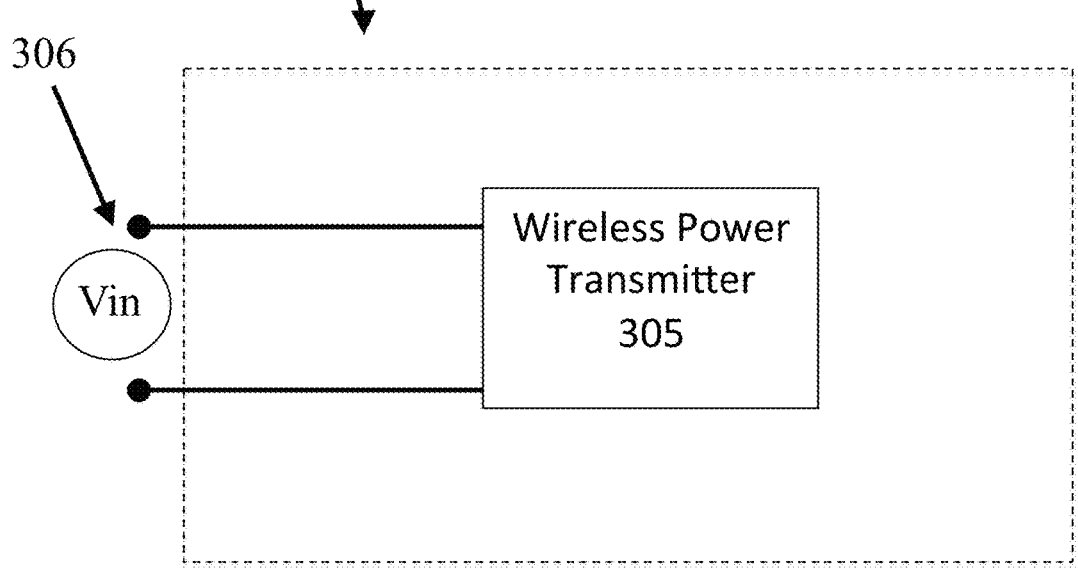
FIG. 3C is a schematic circuit diagram of an embodiment of a docking station for the disclosed device.

The sex toy 201 may include a charging circuit 215. The charging circuit 215 may charge the battery 213. In some embodiments, the charging circuit 215 receives power from a source external to the sex toy 201, and uses the received power to charge the battery 213. The charging circuit 215 may include an inductive charge receiver (not shown), which receives power in the form of a varying magnetic field that induces an electric current in the inductive charge receiver, resulting in a supply of electric power with which the inductive charge receiver may charge the battery 213. In some embodiments, the charging circuit 215 is located near to the back of the housing 206, while the other components are located near to the front of the housing 206; in some embodiments, this placement prevents heat generated by the charging circuit 215 from interfering with the timing or other performance of the other components. The charging circuit 215 may be connected to a thermistor 215a; the thermistor 215a may allow the charging circuit 215 to detect when the battery 213 is heating up too much. The charging circuit 215 may modify power input to the battery in response to the input from the thermistor 215a. Some embodiments of the sex toy 201 includes an on/off switch 216; the on/off switch may be a push-button. In some embodiments, the on/of switch 216 is located within the housing 206, and is activated through the housing; for instance a user may activate a push button by pushing it through the housing if the portion of the housing enclosing the push button is flexible. In some embodiments, as shown in FIG. 2D, the sex toy 201 includes a heart rate sensor 217. The heart rate sensor 217 may record the heart rate of the user wearing the sex toy 201 and transmit that information to the wireless transmitter 203.

In some embodiments, as shown in FIGS. 3A-3F, the system 200 includes a device that provides external power to the sex toy 201. The device may be a docking station 300. In some embodiments, the docking station 300 has a housing 301. The housing 301 may be constructed from any material or combination of materials suitable for the construction of the housing 206 as described above in connection with FIGS. 2A-2C. The housing 301 may include a base 302. The base 302 may be formed so that the docking station 300 rests stably on a flat surface such as a tabletop when placed with the base 302 in contact with the flat surface; the base 302 may be substantially flat. The housing 301 may include an indentation 303 shaped to receive the sex toy 201; in some embodiments, the indentation 303 has a perimeter that complements the perimeter of the sex toy 201, so that the sex toy 201 rests snugly in the indentation 303. The indentation may be formed so that the sex toy 201 only fits in the indentation 303 in a position placing the inductive charge receiver of the sex toy 201 in a substantially optimal position with regard to an inductive charge transmitter 305 as described in further detail below in reference to FIG. 3D. The indentation 303 may be in the upper surface of the housing 301. The housing 301 and indentation 303 may be shaped to permit the ring 202 to protrude from the housing 301 when the sex toy 201 is docked; in some embodiments, this enables a user to remove the sex toy 201 easily from the docking station 300 by grasping the ring 202. As a non-limiting example, the housing 301 may have a semi-circular indentation 304 at the end where the ring 202 is located when the sex toy 201 is docked; the semi-circular indentation 304 may leave the interior of the ring 202 substantially exposed from both sides.

The docking station 300 may include a component that transfers electrical energy to the sex toy 201 when the sex toy 201 is docked in the docking station 300. The component may be a wireless charge transmitter 305. In some embodiments, the wireless charge transmitter 305 is an inductive transmitter, which converts a varying electrical current into a varying magnetic field by means of which the inductive transmitter can transfer electrical power to an inductive charge receiver as described above in reference to FIGS. 2A-2C. In some embodiments, the wireless charge transmitter 205 is positioned within the docking station 300 in a manner that places it in a substantially optimal position opposite the inductive charge receiver of the sex toy 201 when the sex toy 201 is in the indentation 303. The housing 301 and sex toy 201 may be constructed so that the inductive charge receiver and inductive charge transmitter are in close proximity when the sex toy 201 is docked in the docking station 300; in some embodiments, the distance between the inducting charge transmitter and inductive charge receiver is less than 2.3 millimeters (0.091 inches) when the sex toy 201 is docked in the docking station 300. The wireless charge transmitter 305 may be connected to a power input port 306; for instance, the docking station may have a "wall plug" that connects to AC line voltage. The docking station may receive power from a USB cable connected to a power adaptor; the power adaptor may be configured to connect to AC line voltage or to other power sources.

The system 200 may include a computing device 205. The computing device 205 may be any computing device 100 as described above in reference to FIGS. 1A-B. In some embodiments, the computing device 205 is a mobile device, such as a "smartphone" or tablet. In other embodiments, the computing device 205 is a personal computer. The computing device 205 may be configured to receive communication from the wireless communicator 204. In some embodiments, the computing device 205 relays information from the wireless communicator 204 to a server 122.

In some embodiments, an application executes on the computing device 205. The application may be a web application 123 as described above in reference to FIGS. 1A-B. The application may be a mobile application. FIGS. 4A-4F are screenshots illustrating some aspects of the application 400. In some embodiments, the system 200 includes both a mobile application and a web application. In some embodiments, the application 400 includes a navigation bar 401. The navigation bar 401 may enable a user to choose a screen of the application 400 that will display. The navigation bar 401 may include a tab corresponding to each screen the user may select. In some embodiments, the navigation bar 401 includes a "Health" tab. The navigation bar 401 may include a "Fun" tab. The navigation bar 401 may include a "Tips" tab. The navigation bar 401 may include a "History" tab. Some embodiments of the application 400 include a field 402 indicating the date and time of a sexual encounter with regard to which the application 400 is displaying data.

The application 400 may provide one or more fields describing energy expended during a sexual encounter; the user may be able to access the one or more fields by selecting the "health" tab in the navigation bar 401. In other embodiments, the user accesses the one or more fields by selecting a report tile on the main screen of the application. The application 400 may provide a field 405 describing the total effort expended. The total effort expended may be expressed as a total number of moves performed by the wearer of the sex toy 201 during the sexual encounter. The total effort expended may be expressed as the total distance traveled by the sex toy 201 due to the cumulative motion of all sex moves performed during the sexual encounter. The total effort expended may be expressed in terms of calories burned 414. The total effort expended may be expressed in terms of the duration of the sexual encounter 415. In other embodiments, a field 416 may describe the calories burned per minute; this may be continuously or periodically updated during the sexual encounter. A field 417 may enable the user to enter the sexual positions engaged in during the sexual encounter.

The application 400 may provide one or more fields for entertainment purposes concerning the sexual encounter; the user may access these fields by selecting the "fun" tab in the navigation bar 401. In some embodiments, the application 400 provides a field 403 that indicates the velocity of movements performed during the sexual encounter by the person wearing the sex toy 201. The field 403 may indicate the maximum velocity detected during the sexual encounter. The field 403 may indicate the average velocity of the movements performed during the sexual encounter. The velocities may be calculated as described below in connection with FIG. 5. The application 400 may provide a field 404 describing the acceleration the sex toy 201 detected during one or more sexual movements; for instance, the field 404 may describe the maximum acceleration detected. The maximum acceleration may be expressed in multiples of the acceleration exerted by the gravitational field of the earth at sea level, sometimes referred to as "Gs." The application 400 may provide a field 406 to which the user may upload a photograph of the user and partner(s) in the sexual encounter; the field 406 may include a button that activates a camera coupled to the computing device 205, such as the built-in camera of a mobile device.

In some embodiments, the application 400 provides one or more fields permitting users to share and acquire feedback concerning the sexual encounter. The application 400 may provide a field 407 enabling the user to rate the sexual encounter. The field 407 may provide a numerical rating system such as a "star rating" from 1 to 5 stars. The field 407 may provide verbal descriptions that accompany the star rating; for instance, "best sex in a long time" may be the verbal description corresponding to a 4-star rating. The application 400 may provide one or more fields 408 permitting the user to describe what he or she would like to try during the next sexual encounter. For instance, the one or more fields 408 may include a drop-down list with options corresponding to requests for more or less vigorous copulation, for longer or shorter durations, or for more passionate sex, than in the instant sexual encounter. In other embodiments, the one or more fields 408 include a random or pseudo-random generator of options; for instance, the application may display a field that populates with a randomly or pseudo-randomly selected option. As another example, the application may display a circle (not shown) that the user can "spin" using controls; the circle may be graduated with various options, or have an indicator that spins within the circle and settles on an option. In other embodiments, the user can move through the options by turning a circle similarly to a knob on a radio, causing various options to appear above the circle in an analogous manner to browsing through drop-down list.

Figure 4A:
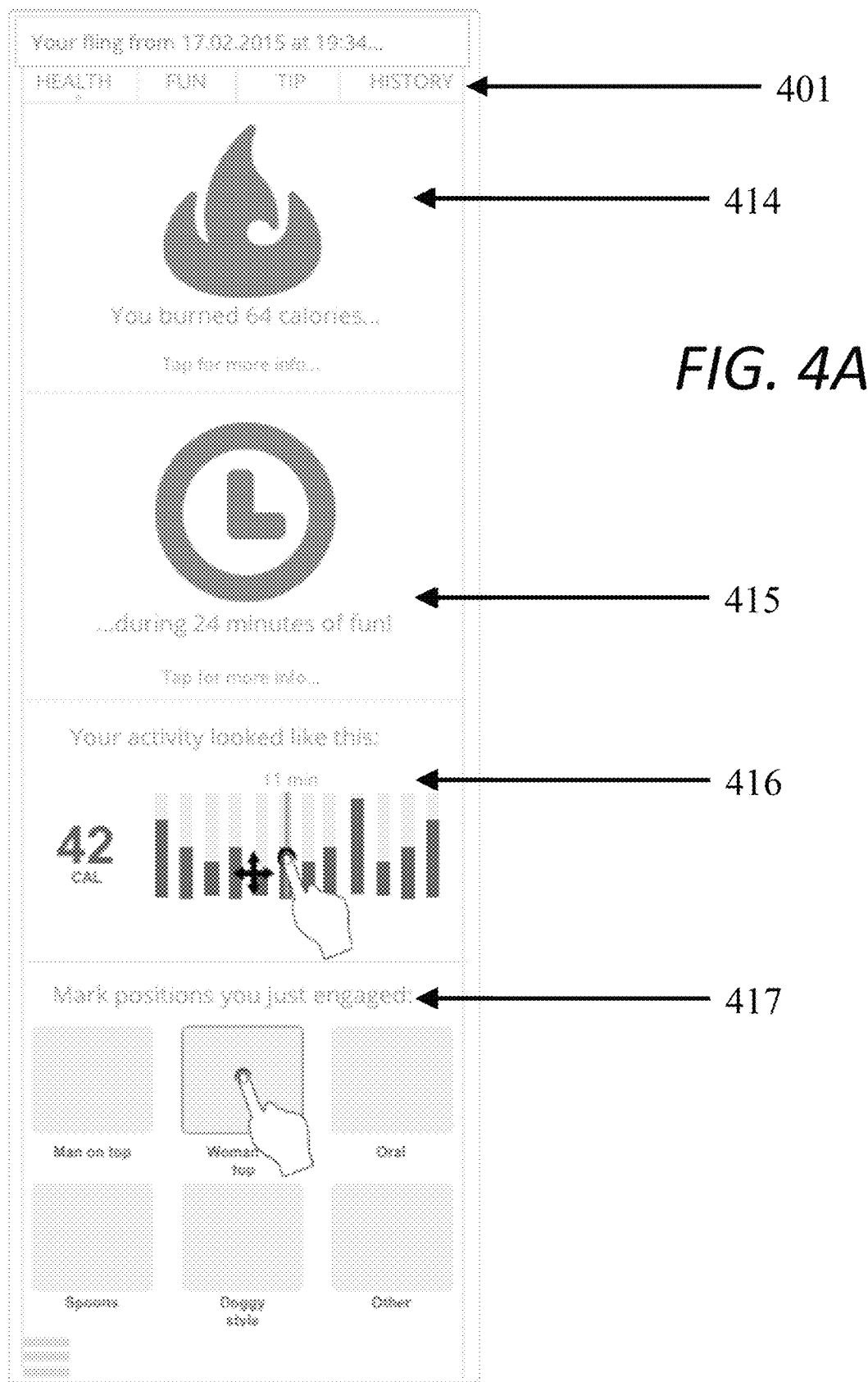
FIG. 4A is a screenshot of an embodiment of an application.
Figure 4D:
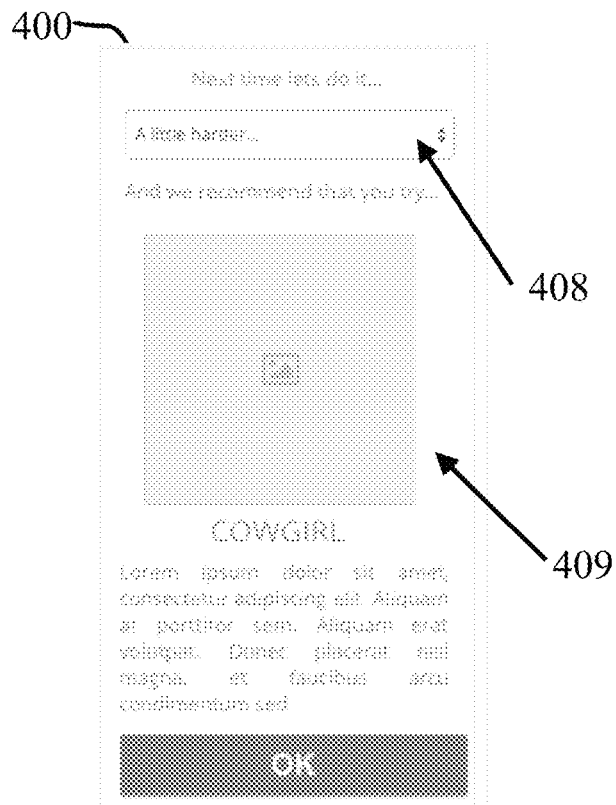
FIG. 4D is a screenshot of an embodiment of an application.
Figure 4E:
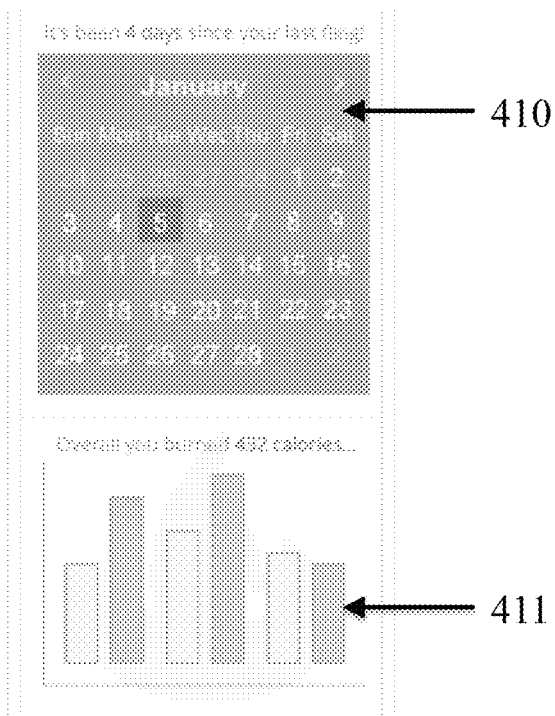
FIG. 4E is a screenshot of an embodiment of an application.
Figure 4F:
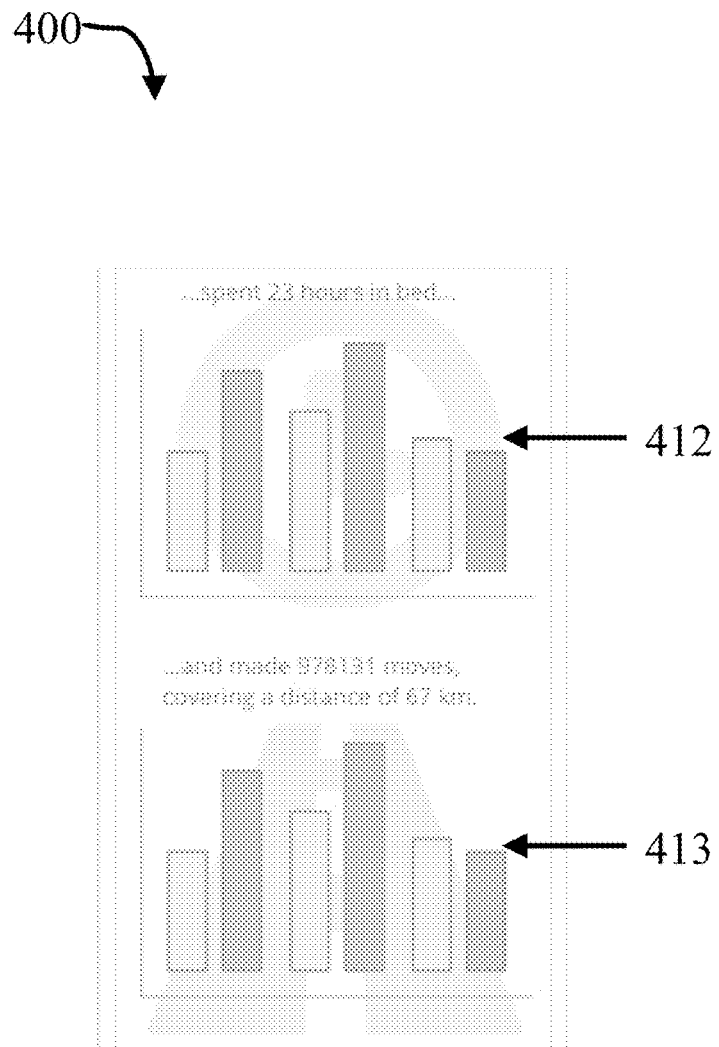
FIG. 4F is a screenshot of an embodiment of an application.
Figure 4G:
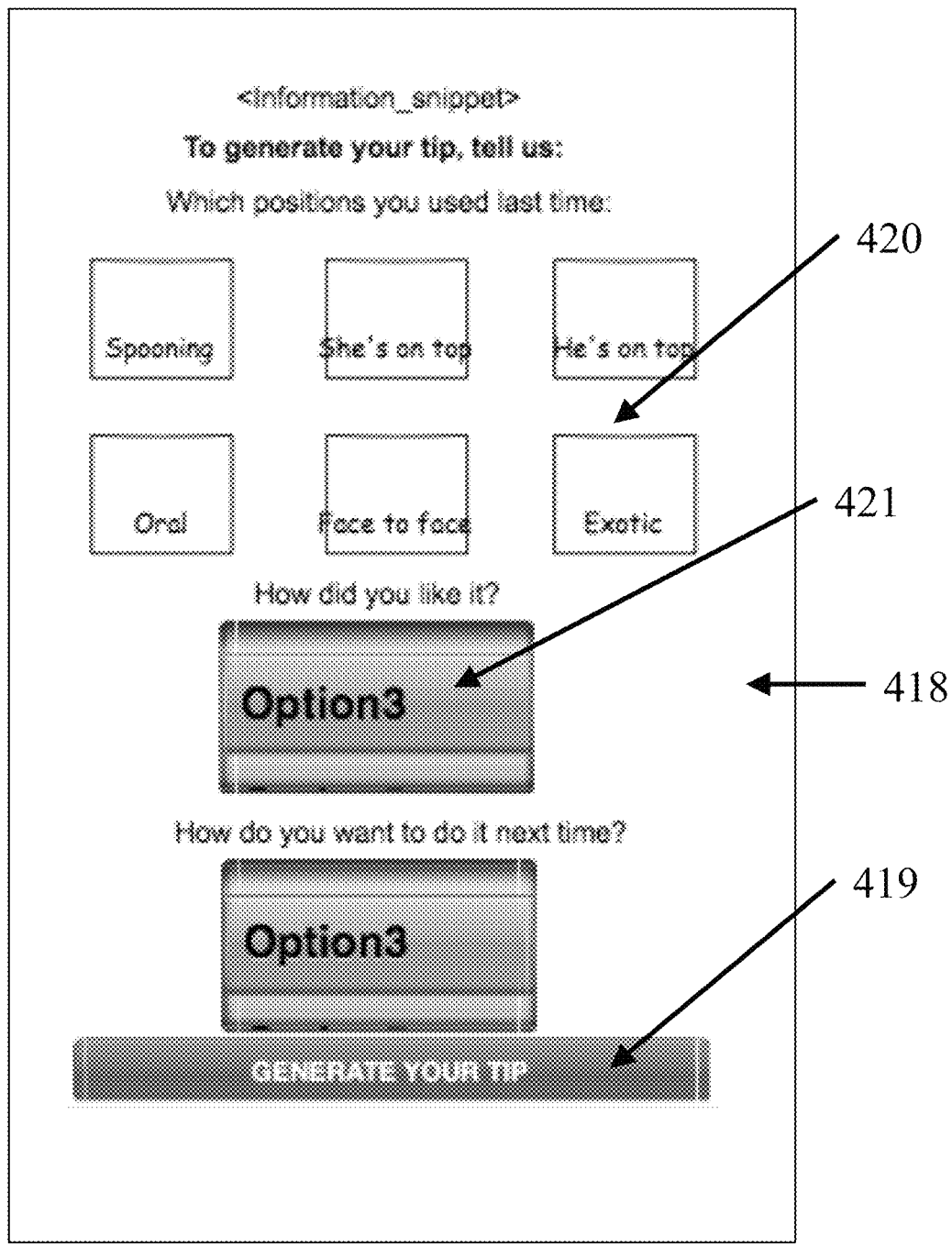
FIG. 4G is a screenshot of an embodiment of an application.

The application 400 may include a field 409 displaying a tip generated as described in further detail below in reference to FIG. 5 for an improved experience. The field 409 may include a description of a sexual position. The field 409 may include at least one picture of a sexual position. The field 409 may include other text or pictures describing possible adjustments for future sexual encounters. In some embodiments, the application 400 sends periodic notifications to the user including additional tips. The notifications may be provided by the user interface of the application 400. The notifications may be provided using electronic communications, which may use any suitable protocol for sending messages by electronic means; for instance, the notifications may be provided via electronic mail (email) using a simple mail transfer protocol (SMTP) or post office protocol (POP). The notifications may be sent using text messaging, such as that sent over the simple messaging service (SMS) protocol. Notifications may also be sent using protocols specific to particular platforms or operating systems used in mobile devices, tablets, or other computing devices. In some embodiments, as shown in FIG. 4G, the application 400 includes a tip request screen 418; the tip request screen 418 may have a control 419 the user can select to request the generation of a tip. The tip request screen 418 may have one or more fields 420 permitting the user to describe sexual positions or techniques employed during the sexual encounter. The tip request screen 418 may have one or more fields 421 the user may use to enter feedback concerning the sexual encounter as described in further detail above; the one or more fields 421 may include a range of options the user can select between, including buttons, drop-down lists, checkboxes, or any other controls.

In some embodiments, the application 400 provides one or more fields describing history of sexual encounters by the user, using the sex toy 201. In some embodiments, the one or more fields describing history are accessed by selecting the "history" tab on the navigation bar 401. The application 400 may provide a calendar 410 highlighting days on which the user had a sexual encounter. The application 400 may provide a graph 411 depicting the overall calories the user has expended engaging in sexual encounters, over a given period of time. In some embodiments, the user is able to select a date range for display; the application 400 may also default to a certain period, such as the entire history of the user's use of the application 400. The application 400 may provide a graph 412 depicting the cumulative time spent engaging in sexual encounters over a given period of time. The application 400 may provide a graph 413 depicting the cumulative number of sexual motions over a given period of time; the graph 413 may depict the total distance traversed by the sex toy 201 in sexual moves over a given period.

The application 400 may provide a messaging service (not shown) for users to communicate concerning past or prospective sexual encounters. The messaging service may use any protocol for electronic communication. The application 400 may be configured to detect an agreement, reached using the messaging service, between users to engage in a sexual encounter.

Figure 5:
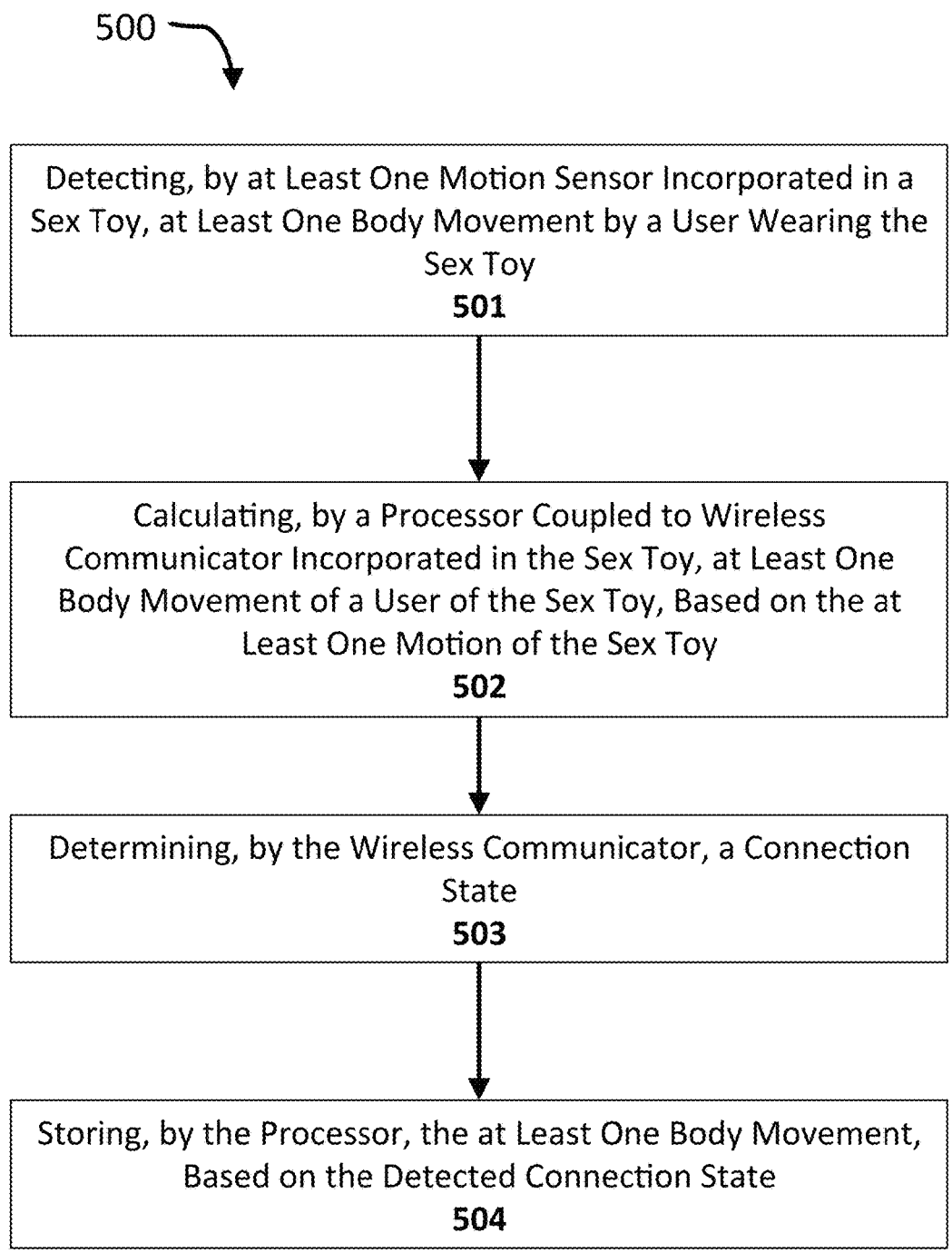
FIG. 5 is a flow chart illustrating one embodiment of the claimed method for tracking sexual movements.

FIG. 5 illustrates some embodiments of a method 500 for tracking sexual movements. The method 400 includes detecting, by at least one motion sensor incorporated in a sex toy, at least one motion of the sex toy (501). The method 400 includes calculating, by a processor coupled to a wireless communicator incorporated in the sex toy, at least one body movement of a user of the sex toy, based on the at least one motion of the sex toy (502). The method 400 includes determining, by the wireless communicator, a connection state (503). The method 500 includes storing, by the processor, the at least one body movement, based on the detected connection state (504).

Referring to FIG. 5 in greater detail, and by reference to FIGS. 2A-4F, the at least one motion sensor 203 detects at least one motion of the sex toy 201 (501). In some embodiments, the at least one motion sensor 203 detects a direction of acceleration; the detection of the direction of acceleration may be accomplished by one or more accelerometers included in the at least one motion sensor 203. In other embodiments, the motion sensor 203 detects a degree of acceleration, for instance using one or more accelerometers included in the at least one motion sensor 203. The at least one motion sensor 203 may detect a change in orientation of the sex toy 201 using at least one gyroscope. The at least one motion sensor 203 may detect the orientation of the sex toy 201 with respect to the magnetic field of the Earth, for instance by using at least one magnetometer.

The processor calculates at least one body movement of a user of the sex toy, based on the at least one motion of the sex toy (502). In some embodiments, the processor coupled to the wireless communicator 204 is incorporated in the wireless communicator 204. In some embodiments, the processor estimates the velocity at which the sex toy 201 moved during the at least one motion of the sex toy 201, by numerically integrating at least one detected acceleration. The processor may store the data describing each of a plurality of detected accelerations in a first-in-first-out (FIFO) buffer, and numerically integrate each detected acceleration; an integration constant representing the most recently calculated velocity may be added to each integration result to calculate the current velocity. In some embodiments, the processor compares the at least one motion to one or more threshold values to determine that a particular sexual movement has taken place. For instance, one threshold value may be a minimum acceleration value. Another threshold value may be a value representing minimum period of time over which the body movement is likely to take place. Another threshold value may be a value representing a maximum time over which the body movement is likely to be taking place. As a non-limiting example, the processor may interpret an acceleration that achieves a maximum value in excess of a threshold amount and that lasts for longer than a minimum amount of time as a single thrust.

The wireless communicator 204 determines a connection state (503). In some embodiments, the wireless communicator 204 determines whether the at least one computing device 205 is within signal range. The wireless communicator 204 may detect a signal from the at least computing device 205. The wireless communicator 204 may attempt to connect to the at least one computing device 205; determining the connection state may involve determining that the wireless communicator 204 has succeeded in connecting to the at least one computing device 205. In some embodiments, each sex toy 201 has a unique identifier that it transmits over the wireless connection; the computing device 205 may match the detected identifier of the sex toy 201 to a particular user, and connect the sex toy 201 to an instance of the application 400 corresponding to that user's user account.

Determining the connection state may involve determining that there is a signal from the at least one computing device 205 but that the wireless communicator 204 has failed to connect to the at least one computing device 205. Determining the connection state may include determining that there is no detected signal from the at least one computing device 205.

The processor stores the at least one body movement, based on the detected connection state (504). In one embodiment, storing the at least one body movement involves storing data describing the at least one body movement. In one embodiment, the detected connection state indicates that there is no connection to the at least one computing device, and the processor stores data in memory 208 incorporated in the sex toy 201. In another embodiment, there is a working connection to the at least one computing device 205, and the processor stores the at least one body movement by transmitting data describing the at least one body movement to the at least one computing device 205. In some embodiments, upon detection of a working connection to the at least one computing device 205 by the wireless communicator 204, the processor determines that a series of body movements are stored in the memory 208; the processor may transmit the stored series of body movements to the at least one computing device 205. The processor may delete the series of body movements from the memory 208 after successfully transmitting the series of body movements to the at least one computing device 205. In some embodiments, the sex toy 201 saves data concerning a sexual encounter in memory 208 during the sexual encounter, and transmits the data to the computing device 205 when the sexual encounter concludes; for instance, the data may be sent when the sex toy 201 is switched off using the on/off switch 216.

Some embodiments of the method 500 further involve calculating, by the at least one computing device 205, at least one cumulative datum concerning the sexual encounter, using the at least one body movement. In some embodiments, the at least one computing device 205 calculates the total calories burned by a user during the sexual encounter. The at least one computing device 205 may use one or more user-specific data to calculate the calories burned in a particular body move. The user-specific data may include the user's weight. The user-specific data may include the user's age. The user-specific data may include the user's height. The user-specific data may include the user's gender. The at least one computing device 205 may calculate the calories burned in a body movement using data concerning the body movement itself. The data concerning the body movement may include the velocity of the body movement. The data concerning the body movement may include the speed of the body movement. The data concerning the body movement may include the force of the body movement. The data concerning the body movement may include the duration of the body movement. The calculation may include data from one or more clinical studies concerning the energy expended by a person performing a body movement as a function of the user-specific data and the data concerning the body movement. The data may concern the likely energy expended by a sexual partner of the person. In some embodiments, the computing device 205 aggregates the calories spent for all body motions recorded during a sexual encounter to determine the total calories burned by the user during the sexual encounter.

In some embodiments, the at least one computing device 205 calculates the duration of the sexual encounter. The at least one computing device 205 may calculate the duration of the sexual encounter by determining when the sex toy 201 was switched on to begin the sexual encounter, determining when the sex toy 201 was switched off to end the sexual encounter, and calculating the difference between the second and first times. In some embodiments, the computing device 205 determines the calories burned per minute by the user; the sex toy 201 may allocate movement data to each minute of the sexual encounter and send it to the at least one computing device 205.

The computing device 205 may calculate the top speed achieved by the user of the sex toy 201, by comparing the maximal speed of each movement to each other movement to determine an overall maximum speed. The computing device 205 may calculate the average speed of the movements performed by the person wearing the sex toy 201 by averaging determined velocities from the sexual encounter; in one embodiment, the average is over all motions engaged in during the sexual encounter. The computing device 205 may determine the maximal acceleration achieved during the sexual encounter; this may be achieved by determining the maximal acceleration of each detected body movement, and comparing the maximal accelerations to determine the overall maximum. The computing device 205 may estimate the number of thrusts the user of the sex toy 201 has made during the sexual encounter; the computing device 205 may calculate the number of thrusts by enumerating the number of thrusts detected by the at least one motion sensor 203.

The computing device 205 may calculate the total calories burned during all sexual encounters the user of the sex toy 201 engaged in over a certain period of time; in some embodiments the computing device 205 adds together the total calories burned from each sexual encounter. The computing device 205 may calculate the total amount of time the user has spent engaging in sexual encounters using the sex toy 201, for instance by aggregating the durations of all sexual encounters engaged in using the sex toy 201 during that period. The computing device 205 may determine the number of detected body motions from all sexual encounters during a certain period, for instance by adding together the enumerated body motions from each sexual encounter to produce a cumulative sum.

Although for the sake of simplicity, the above calculations of cumulative data are described as performed by the computing device, 205, each may also be performed by the processor in the sex toy 201; in other words, the computing device performing each of the cumulative data calculations may be the sex toy 201 itself.

In some embodiments, the computing device 205 displays data to the user; the computing device 205 may display the data using the application 400. The displayed data may include data concerning the at least one determined body motion. The displayed data may include the one or more cumulative data described above in reference to FIG. 5.

In some embodiments, the computing device 205 generates a user tip using at least one datum of the data concerning the at least one body movement data and the cumulative data. The computing device 205 may generate the tip using user-entered data. For instance, where the user has entered data indicating that the user wanted a gentler experience, the computing device 205 may determine the average acceleration, peak acceleration, or both and generate a tip that proposes a solution that gives the couple possibility of reaching lower force and speed; the computing device 205 may generate a tip that suggests a sexual position conducive to more gentle sexual movements. In other embodiments, the computing device 205 compares facts concerning a plurality of sexual encounters to user ratings, and determines one or more features of a preferred sexual encounter for that user; for instance, if sexual encounters that the user rates highly always last for longer than a certain duration, and the most recent sexual encounter was of shorter duration and was rated lower, the computing device 205 may produce a tip suggesting a longer duration for future sexual encounters. The computing device 205 may receive a user instruction describing at least one sexual position the user has used in at least one sexual encounter; the computing device 205 may determine that a particular sexual position is associated with high ratings by the user, and propose that position for a future sexual encounter. The computing device 205 may maintain a data structure containing various sexual positions and information relating them by degree of similarity; the computing device 205 may create a tip proposing a sexual position from the data structure that is similar to a sexual position associated with past highly-rated sexual encounters. Likewise, if the user has entered an instruction on the application 400 indicating a desire for a more passionate sexual encounter, the computing device 205 may generate a tip suggesting a sexual position consistent with a greater degree of passion. The computing device 205 may maintain a database containing information concerning past sexual encounters.

In some embodiments, the computing device 205 combines information concerning the sexual encounter with geographic information. For instance, where the computing device 205 has a navigation facility as described above in reference to FIGS. 1A-B, the computing device 205 may combine the location of the computing device at the time of the sexual encounter with data concerning the sexual encounter; as a non-limiting example, the computing device 205 may create a virtual map with a "pin" indicating the location of the sexual encounter. Selection of the pin may enable users to view details concerning the sexual encounter. In some embodiments, the computing device 205 provides the user with a prompt asking for the user's permission to combine geographic information with the sexual encounter information; the computing device 205 may combine the geographic information with the sexual encounter information only if it receives a user instruction indicating the user's approval. The user may also enter an instruction indicating which users are permitted to view information concerning the sexual encounter. For instance, the pin on the virtual map may be visible to the user only, to the user and a partner to the sexual encounter only, to a group of people designated by the user, or to the general public.

In some embodiments, the computing device 205 conveys the data from one or more sexual encounters to a server 122. The server 122 may analyze sexual encounter data of multiple users, to produce a superior user experience; for instance, the data may be analyzed to produce superior tips. The data may be analyzed to produce better communication between the sex toy 201, the application 400, and users. The server 122 may compare ratings tied to sex characteristics of populations of users, and search for connections between ratings, user attributes, and attributes associated with particular sexual encounters. For instance, the selection of sexual positions for tips may be weighted by average user rating. As another example, the server 122 may detect that couples that want a gentler sex do not enjoy a particular position that the application 400 has been suggesting and might transmit information to the application 400 indicating that it should recommend a different sexual position to users who want a gentler experience. The sexual encounter data analyzed by the server 122 may be anonymized, by removing all information usable to identify a particular user prior to analysis. In some embodiments, the computing device 205 requests user permission prior to transmitting the data to the server 122; the computing device 205 may transmit the data only upon receiving user authorization.

In some embodiments, the wireless communicator 204 senses that a computing device 205 is within signal range, and sending a user alert. The user alert may be sent by activating the light source 212. The signal may be sent by activating the vibrator 209. The signal may be sent by communicating a message to the at least one computing device 205. As a non-limiting example, the sex toy 201 may glow with a green light when the sex toy 201 is charging. When sex toy 201 is fully charged it may not blink or glow at all. When the user turns the sex toy 201 on it may blink red three times. When sex toy 201 is in the docking station, it may attempt to incentivize a nearby user to have sex by blinking slowly with a red light. In another embodiment, when the application 400 detects that two users have agreed to engage in a sexual encounter, the sex toy 201 may cause its light source to blink quickly with a red light. In other embodiments, a light source 310 is incorporated in the docking station, rather than the sex toy 201; the light source may indicate charging status or any of the other indications described above for the light source in the sex toy 201.

In one embodiment, the sex toy 201 is manufactured by a molding method. The method of manufacture may involve assembling the electronic components of the sex toy 201. In some embodiments, the electronic components are assembled by connecting some of the components together on a printed circuit board. The components may be assembled by connecting some components together using wires. The manufacture method may include placing the electrical components within a plastic shell. The manufacture method may include placing the plastic shell in a mold, and adding material into the mold to form the housing 206 and ring 203.

It will be understood that the system and method may be embodied in other specific forms without departing from the spirit or central characteristics thereof. The present examples and embodiments, therefore, are to be considered in all respects as illustrative and not restrictive, and the system method is not to be limited to the details given herein.

What is claimed is:

1. A method for tracking sexual movements, the method comprising:
    detecting, by at least one motion sensor incorporated in a sex toy, at least one motion of the sex toy;
    calculating, by a processor coupled to a wireless communicator incorporated in the sex toy, at least one body movement of a user of the sex toy, based on the at least one motion of the sex toy;
    determining, by the wireless communicator, a connection state to at least one computing device;
    storing, by the processor, in a memory incorporated in the sex toy, the at least one body movement, based on the detected connection state.

2. The method of claim 1, wherein the detecting further comprises detecting a direction of acceleration of the sex toy.

3. The method of claim 1, wherein the detecting further comprises detecting a degree of acceleration of the sex toy.

4. The method of claim 1, wherein the detecting further comprises detecting a change in orientation of the sex toy.

5. The method of claim 1, wherein the calculating further comprises:
    maintaining a number representing a current velocity of the sex toy;
    numerically integrating a detected acceleration to calculate a resulting velocity; and
    adding the resulting velocity to the number representing the current velocity.

6. The method of claim 1, wherein the calculating further comprises comparing the at least one motion to one or more threshold values to determine that a particular sexual movement has taken place.

7. The method of claim 1, wherein the determining further comprises determining that there is no connection to the at least one computing device, and wherein the storing further comprises storing the at least one body movement in the memory incorporated in the sex toy.

8. The method of claim 1, wherein the determining further comprises determining that there is a connection to the at least one computing device, and wherein the storing further comprises transmitting data describing the at least one body movement to the at least one computing device.

9. The method of claim 8, wherein the determining further comprises determining that a series of body movements are stored in memory of the sex toy; and wherein the storing further comprises
    transmitting the stored series of body movements to the at least one computing device.

10. The method of claim 8 further comprising:
    saving data concerning a sexual encounter in the memory incorporated in the sex toy during the sexual encounter; and
    transmitting the data to the computing device when the sexual encounter concludes.

11. The method of claim 8 further comprising calculating, by the at least one computing device, at least one cumulative datum concerning a sexual encounter, using the at least one body movement.

12. The method of claim 11, wherein the calculating the cumulative datum further comprises calculating total calories burned by the user during the sexual encounter.

13. The method of claim 11, wherein the calculating the cumulative datum further comprises calculating a duration of the sexual encounter.

14. The method of claim 11, wherein the calculating the cumulative datum further comprises calculating a top speed achieved by the user of the sex toy.

15. The method of claim 11 further comprising generating, by the computing device, a user tip using at least one datum of the data concerning the at least one body movement data and the at last one cumulative datum.

* * * * *